United States Patent
Sbragia et al.

[11] Patent Number: 5,945,453
[45] Date of Patent: Aug. 31, 1999

[54] BENZOYLPHENYLUREA INSECTICIDES TO CONTROL COCKROACHES

[75] Inventors: Ronald J. Sbragia, Placerville, Calif.; George W. Johnson, Indianapolis; Laura L. Karr, Lebanon, both of Ind.; Jeff M. Edwards, Torrington, Wyo.; Brian M. Schneider, Carmel, Ind.

[73] Assignee: Dow AgroSciences LLC, Indianapolis, Ind.

[21] Appl. No.: 08/961,893

[22] Filed: Oct. 31, 1997

Related U.S. Application Data

[60] Provisional application No. 60/029,747, Nov. 8, 1996.

[51] Int. Cl.$^6$ .......................... C07C 275/54; A01N 47/30
[52] U.S. Cl. ............................................... 514/594; 564/44
[58] Field of Search ................................ 514/594; 564/44

[56] References Cited

U.S. PATENT DOCUMENTS

| | | | |
|---|---|---|---|
| 3,748,356 | 7/1973 | Wellinga et al. | 260/553 E |
| 4,468,405 | 8/1984 | Rigterink et al. | 424/322 |
| 4,798,837 | 1/1989 | Drabek et al. | 514/594 |
| 4,925,875 | 5/1990 | Drabek | 514/594 |
| 4,925,876 | 5/1990 | Drabek | 514/594 |
| 4,973,589 | 11/1990 | Barnett et al. | 514/245 |
| 5,132,325 | 7/1992 | Drabek et al. | 514/594 |
| 5,153,224 | 10/1992 | Drabek et al. | 574/594 |
| 5,288,756 | 2/1994 | Drabek et al. | 514/594 |
| 5,416,102 | 5/1995 | Barnett et al. | 514/351 |
| 5,556,883 | 9/1996 | Thoms et al. | 514/594 |

FOREIGN PATENT DOCUMENTS

| | | |
|---|---|---|
| A-68094/87 | 8/1987 | Australia . |
| 87/71748 | 10/1987 | Australia . |
| 194688 | 9/1986 | European Pat. Off. . |
| 221847 A2 | 5/1987 | European Pat. Off. . |
| 0243790 A1 | 11/1987 | European Pat. Off. . |
| 263438 A2 | 4/1988 | European Pat. Off. . |
| 290392 A1 | 11/1988 | European Pat. Off. . |
| 3827133 A1 | 2/1989 | Germany . |
| 2166134 | 4/1986 | United Kingdom . |
| WO 94/03066 | 2/1994 | WIPO . |
| WO 95/16354 | 6/1995 | WIPO . |

OTHER PUBLICATIONS

Journal of Economic Entomology (Oct., 1996), vol. 89, No. 5, pp. 1156–1160, Nan–Yao Su and Rudolf H. Scheffrahn, "Comparative Effects of Two Chitin Synthesis Inhibitors, Hexaflumuron and Lufenuron, in a Bait Matrix Against Subterranean Termites (Isoptera:Rhinotermitidae)".

*Primary Examiner*—Phyllis G. Spivack
*Attorney, Agent, or Firm*—Donald R. Stuart

[57] ABSTRACT

Compounds of the formula (I)

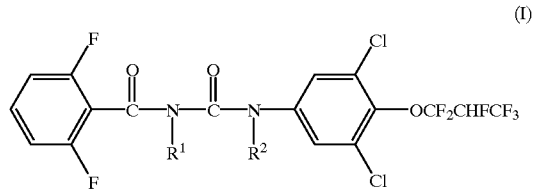

wherein $R^1$ and $R^2$ are H, methyl, or ethyl, and wherein at least one of $R^1$ and $R^2$ is methyl or ethyl, are disclosed to control cockroaches.

4 Claims, No Drawings

BENZOYLPHENYLUREA INSECTICIDES TO CONTROL COCKROACHES

CROSS REFERENCE TO RELATED APPLICATION

This patent application claims the benefit of Provisional U.S. patent application Ser. No. 60/029,747 filed Nov. 8, 1996.

BACKGROUND OF THE INVENTION

This invention provides novel benzoylphenylurea insecticides and novel methods of controlling cockroaches, ants, fleas, and termites.

A broad class of benzoylphenylurea insecticides is disclosed in U.S. Pat. No. 3,748,356. European patent application 263438 discloses that certain N-substituted phenyl-N'-substituted benzoyl-N-methylureas are highly safe to beneficial aquatic Crustacea while exhibiting equal or superior insecticidal activities to non-alkylated analogs. Hexaflumuron, a commercially significant benzoylphenylurea, is disclosed in U.S. Pat. No. 4,468,405. Use of hexaflumuron in methods of controlling termites is disclosed in WO 93/24011. Use of hexaflumuron to control cockroaches is disclosed in WO 94/03066. The compound N-[3,5-Dichloro-4-(1,1,2,3,3,3-hexafluoropropoxy)phenyl]-N'-(2,6-difluorobenzoyl) urea is disclosed U.S. Pat. No. 5,288,756 and its use to prevent reinfestation of cats and dogs by fleas is disclosed in U.S. Pat. No. 5,416,102, but there was no disclosure of the unexpected activity of the compound against cockroaches, ants, fleas, and termites.

We have discovered that certain benzoylphenylurea compounds, some of which are novel, have substantially greater activity against cockroaches, ants, fleas, and termites than would have been expected based on comparison with the closest prior art, i.e., hexaflumuron. Another significant property of the novel compounds of the invention is their surprisingly low toxicity to Daphnia.

SUMMARY OF THE INVENTION

The invention provides a method of controlling cockroaches, ants, fleas, or termites which comprises delivering a effective amount of a compound of the formula (I):

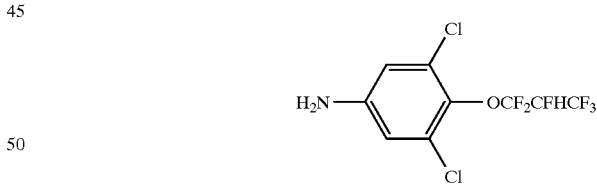

wherein $R^1$ and $R^2$ are H, methyl, or ethyl, to a location where control of cockroaches, ants, fleas, and termites is desired.

The invention also provides novel compounds of the formula (II)

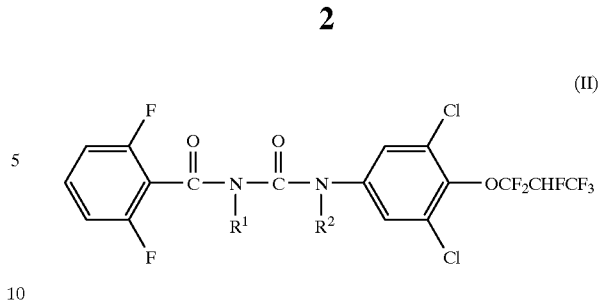

wherein $R^1$ and $R^2$ are H, methyl, or ethyl, provided that at least one of $R^1$ and $R^2$ is methyl or ethyl.

DETAILED DESCRIPTION OF THE INVENTION

Intermediate 1: 2,6-difluorobenzoyl isocyanate

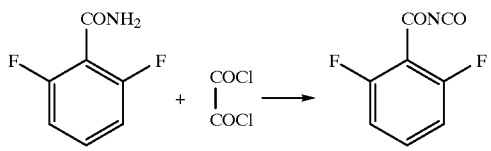

A mixture of 0.52 g of 2,6-difluorobenzamide and 0.33 ml of oxalyl chloride was stirred under reflux in 15 mL 1,2-dichloroethane overnight. Solvent was removed under vacuum and 10 mL 1,2-dichloroethane was added. Solvent was removed under vacuum to leave the title intermediate, which could be used directly or dissolved in 1,2-dichloroethane and stored for future use.

Intermediate 2: 3,5-Dichloro-4-(1,1,2,3,3,3-hexafluoropropoxy)aniline

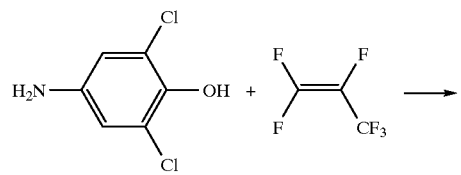

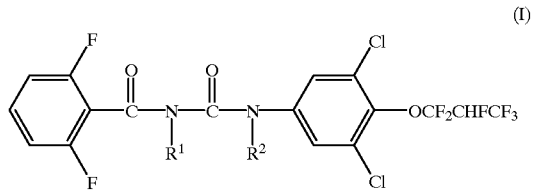

To a solution of 2.0 g of 4-amino-2,6-dichlorophenol in 40 mL tetrahydrofuran at room temperature was added 0.7 g of 87% potassium hydroxide. The mixture was warmed to 40° C. and stirred for 10 minutes, then chilled to 0° C. Hexafluoropropene was bubbled in for 5 minutes, and the mixture stirred at room temperature over night. It was then concentrated under vacuum to dryness. The residue was dissolved in 50 mL dichloromethane and washed with 20 mL brine solution. The organic layer was separated and filtered through phase separation filter paper and then concentrated under vacuum to an oil. This was diluted with 50 mL dichloromethane and 50 mL heptane and re concentrated to give 3.05 g of 3,5-Dichloro-4-(1,1,2,3,3,3- hexafluoropropoxy)aniline as a brown oil. Proton and $^{19}$F nmr spectra were consistent with the proposed structure.

Intermediate 3: 3,5-Dichloro-4-(1,1,2,3,3,3-hexafluoropropoxy)-N-ethyl aniline

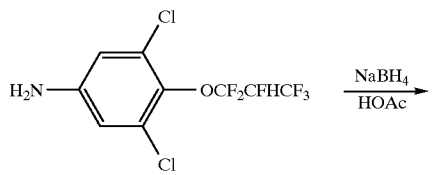

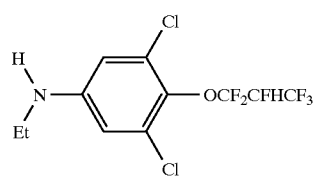

To a solution of 0.33 g 3,5-dichloro-4-(1,1,2,3,3,3-hexafluoropropoxy)aniline in 8 mL glacial acetic acid under an atmosphere of nitrogen at room temperature was slowly added 0.38 g sodium borohydride over a 1.5 hour period through a solid addition funnel between 18–20° C. with ice water cooling. Analysis by thin layer chromatography silica gel 1:1 heptane/ethyl acetate indicated an incomplete reaction. After warming the reaction mixture at 30° C. for two hours, analysis by TLC showed only a faint spot remaining for the starting aniline. The reaction mixture was then added to 100 mL water and the pH was carefully adjusted to 7 by adding solid sodium carbonate. The product was extracted into ethyl acetate 2×80 mL. The ethyl acetate extracts were combined, washed with brine, then dried over magnesium sulfate. The magnesium sulfate was removed by filtering, and the filtrate was concentrated under vacuum to give a brown oil 0.30 g. Chromatograph using a Michel-Miller low pressure silica gel column and elute with 6:1 heptane/ethyl acetate. Pool like fractions and concentrate under vacuum to give 3,5-Dichloro-4-(1,1,2,3,3,3-hexafluoropropoxy)-N-ethyl aniline as a colorless oil 0.17 g. Proton nmr and mass spectra were consistent with the proposed structure. $^{1}$H-NMR d 1.20 (t, 3H), 3.08 (q, 4H), 3.69 (bs, 1H), 4.92–5.22 (md, 1H), 6.48 (s, 2H). MS (CI) m/z 336 (100), 356 (M+H, 100), 384 (M+29, 46).

Preparation of Products

Compound 1: N-[3,5-Dichloro-4-(1,1,2,3,3,3-hexafluoropropoxy)phenyl]-N'-(2,6-difluorobenzoyl) urea

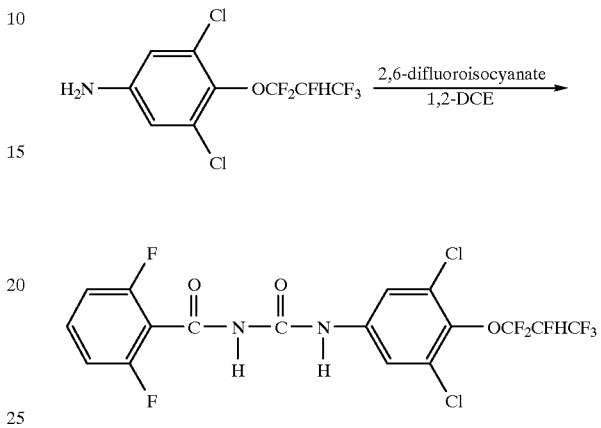

To a solution of 5.13 g 3,5-dichloro-4-(1,1,2,3,3,3-hexafluoropropoxy)aniline in 100 mL 1,2-dichloroethane under an atmosphere of nitrogen at room temperature was added 3.44 g 2,6-difluorobenzoyl isocyanate dissolved in 50 mL dichloroethane dropwise over a 20 minute period between 24°–36° C. with no external cooling. The mixture was heated at 44° C. for 30 minutes. A precipitate formed. The mixture was concentrated under vacuum to dryness and then dissolved in 80 mL boiling methanol. The mixture as filtered and the filtrate concentrated to 30 mL and allowed to cool as product crystallized. Filtration recovered 6.11 g of the title product as a white solid, mp 164–5° C. The proton and $^{19}$F nmr spectra were consistent with the proposed structure. Anal. calcd $C_{17}H_8Cl_2F_8N_2O_3$: C,39.94;H,1.58;N, 5.48. Found: C,39.95;H,1.60;N, 5.49.

Compound 2: N-[3,5-Dichloro-4-(1,1,2,3,3,3-hexafluoropropoxy)phenyl]-N'-(2,6-difluorobenzoyl)-N'-ethyl urea

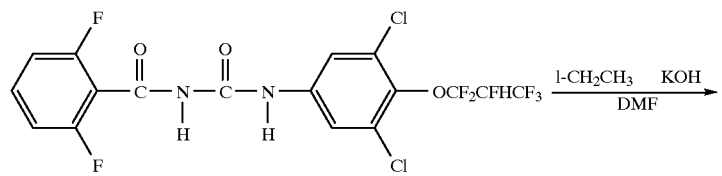

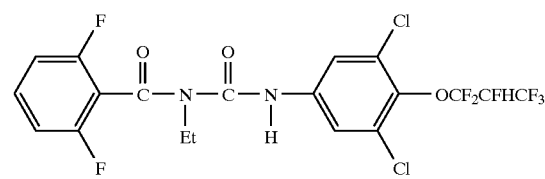

To a solution of 5.00 g N-[3,5-dichloro-4-(1,1,2,3,3,3-hexafluoro-propoxy)phenyl]-N'-(2,6-difluorobenzoyl) urea in 10 mL N,N-dimethylformamide was added 0.69 g 87% potassium hydroxide. The mixture was chilled to 5° C. and 3.05 g of iodoethane were added. After stirring the mixture at 5° C. for one hour, analysis by thin layer chromatography silica gel dichloromethane showed a single product forming with a substantial amount of starting material present. The mixture was allowed to warm to room temperature and was stirred at room temperature for 1.5 hour. Analysis by TLC showed multiple product spots. The mixture was poured into 50 mL brine solution and the pH adjusted to 7.0 with 1N hydrochloric acid. The product was extractred into 80 mL ethyl acetate. The organic layer was separated and dried over magnesium sulfate. Magnesium sulfate was removed by filtration and the filtrate was concentrated under vacuum to give 5.85 g. of an oil. This was chromatographed using a Michel-Miller low pressure silica gel column eluted with 2:1 heptane/dichloromethane. Like fractions were pooled and concentrated under vacuum to give the title compound as a white solid 0.46 g, mp 109–11° C. Proton nmr and mass spectra were consistent with the proposed structure. Anal. calcd $C_{19}H_{12}Cl_2F_8N_2O_3$: C,42.32;H,2.24;N,5.20. Found: C, 42.38;H,2.27;N,5.16.

Compound 3: N-[3,5-Dichloro-4-(1,1,2,3,3,3-hexafluoropropoxy)phenyl]-N'-(2,6-difluorobenzoyl)-N-ethylurea

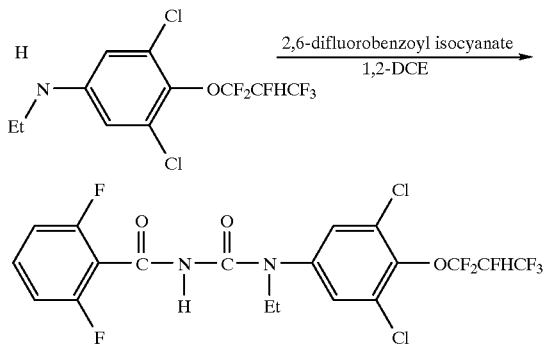

To a solution of 0.17 g 3,5-dichloro-4-(1,1,2,3,3,3-hexafluoropropoxy)-N-ethyl aniline in 0.5 mL 1,2-dichloroethane under an atmosphere of nitrogen at room temperature was added 0.11 g 2,6-difluorobenzoyl isocyanate dissolved in 1.1 mL dichloroethane dropwise over a 5 minute period. The mixture was stirred and warmed to 40° C. for a 2 hour period. Analysis by thin layer chromatography silica gel 4:1 heptane/ethyl acetate indicated no starting aniline remaining. The mixture was stirred at room temperature over night, then concentrated under vacuum to an oil (0.28 g) which solidified. This was chromatographed using a Michel-Miller low pressure silica gel column eluted with 5% ethyl acetate/dichloromethane. Like fractions were pooled and concentrated under vacuum to a white solid 0.11 g, mp 130–33° C. Proton nmr and mass spectra were consistent with the proposed structure. Anal. calcd $C_{19}H_{12}Cl_2F_8N_2O_3$: C,42.32; H, 2.24; N,5.20. Found: C,42.47;H,2.23; N, 5.08.

Biological Activity

German cockroach 2nd instars (*Blattella germanica*)

Continuous, low-dose ingestion exposure (treated cornmeal)

Rates: 0.19, 0.78, 3.12, 12.5, 50, 200 ppm

|  | $LC_{50}$ (ppm) | |
|---|---|---|
|  | 21 days | 42 days |
| Compound 1 | 14.5 | <0.23 |
| Compound 2 | 9.3 | 5.4 |
| Compound 3 | 1.3 | 0.78 |
| hexaflumuron | >200 | >200 |

Under continuous exposure, Compounds 1, 2, and 3 were all far superior to hexaflumuron.

German cockroach 2nd instars (*Blattella germanica*)

Limited ingestion exposure (48 hr) to treated cornmeal

Rates: 1, 10, 100, 1000, 10000 ppm

|  | $LC_{50}$ (ppm) | | | |
|---|---|---|---|---|
|  | 21 days | | 42 days | |
| Compound | low | high | low | high |
| Compound 1 | <1.0 | 52.7 | <1.0 | 30.1 |
| Compound 2 | 192.0 |  | (in progress) |  |
| Compound 3 | 52.2 |  | 30.9 |  |
| hexaflumuron | >10,000 |  | >10,000 |  |

Under limited exposure, Compounds 1, 2, and 3 were far more potent than hexaflumuron.

Cat Flea (*Ctenocephalides felis*)

Continuous exposure of larvae to treated media, impact on subsequent adult emergence Rates: 0.1, 1.0, 10, 1000 ppm

|  | $LC_{50}$ (ppm) | $LC_{90}$ (ppm) |
|---|---|---|
| Compound 1 | 8.6 | 12.8 |
| Compound 2 | 329.4 | >1000 |
| Compound 3 | 78.0 | 460.7 |
| hexaflumuron | 65.7 | 333.5 |

Compound 1 was far more active against fleas than was hexaflumuron.

Subterranean Termite (*Reticulitermes flavipes*)

Continuous exposure (56 days) to treated paper

Rates: 0.78, 3.12, 12.5, 50, 200 ppm

|  | $LC_{50}$ (ppm) | | $LT_{50}$ (days) for |
|---|---|---|---|
| Compound | 21 days | 35 days | 200 ppm trt |
| Compound 1 | >200 | <0.78 | 32.9 |
| Compound 2 | >200 | 22.5 | 34.6 |
| Compound 3 | not run | not run |  |
| hexaflumuron | >200 | <0.78 | 25.7 |

Under continuous exposure against the Eastern Subterranean termite, no performance advantage for Compounds 1, 2, and 3 over hexaflumuron was noted Subterranean Termite (*Reticulitermes virginicus*)
Continuous exposure (56 days) to treated paper
Rates: 0.78, 3.12, 12.5, 50, 200 ppm

| Compound | $LC_{50}$ (ppm) 21 days | $LC_{50}$ (ppm) 35 days | $LT_{50}$ (days) for 200 ppm trt |
|---|---|---|---|
| Compound 1 | 3.5 | <0.78 | 10.2 |
| Compound 2 | not run | not run | |
| Compound 3 | 62.4 | <0.78 | 9.7 |
| hexaflumuron | 28.8 | <0.78 | 16.3 |

Under continuous exposure against Southeastern subterranean termite, both compounds 1 and 3 were faster acting that hexaflumuron, and Compound 3 was more potent at 21 days of exposure.

Subterranean Termite (*Reticulitermes flavipes*)

Limited exposure (7 days) with mortality determined at 14, 28, 42, and 56 days

| Compound | $LT_{50}$ (days) for 10000 ppm treatment |
|---|---|
| Compound 1 | 34.5 |
| hexaflumuron | 32.9 |

Under limited exposure to termites, Compound 1 and hexaflumuron were comparable in speed of activity Ant Studies Laboratory ant bait studies were carried out with Red Imported Fire Ant (RIFA) (*Solenopsis invicta*) and Pharaoh Ant (*Monomorium pharaonis*). Chitin synthesis inhibitors, such as the compounds of the invention, control ants by killing the molting larvae and/or pupae and potentially preventing the hatching of eggs. Because adult workers are not affected, control is measured by effects on the brood.

The studies involved 3–4 day exposure to bait. These limited exposure studies more accurately represent real world bait availability than continuous exposure.

| Compound | Concentration tested | Species | Time to Achieve 50% Brood Reduction* | Time to Achieve 90% Brood Reduction* |
|---|---|---|---|---|
| Compoud 1 | 0.1% | RIFA | 2–3 wks | 4 wks |
| | 0.1% | Pharaoh | 2 wks | 4 wks |
| Hexaflumuron | 0.1% | RIFA | NA | NA |
| | 0.25% | RIFA | 4 wks | 10 wks |
| | 0.1% | Pharaoh | NA | NA |

*Value represents best results achieved with compound.
NA = did not achieve specified percent brood reduction.

Compound 1 is significantly more potent than hexaflumuron based on a short exposure study with RIFA.

Activity against Daphnia
48 hr exposure to treated water

| Compound | $LC_{50}$ (ppb) in water |
|---|---|
| Compound 1 | 12.6 |
| Compound 2 | >100 |
| Compound 3 | >100 |
| hexaflumuron | 68.1 |

Compounds 2 and 3, the alkylated derivatives of Compound 1, were far less active against Daphnia than were Compound 1 or hexaflumuron.

Formulations

In order to facilitate the application of the compounds of formula (I) to the desired locus, or to facilitate storage, transport or handling, the compound is normally formulated with a carrier and/or a surface-active agent.

A carrier in the present context is any material with which the compound of formula (1) (active ingredient) is formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar, paper products, cotton linter, or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone; oils derived from plants, such as corn oil and peanut oil. Mixtures of different liquids are often suitable, for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sufonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide.

Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a suitable food source, such as sawdust for termites or grain or meal for cockroaches, with an amount of active ingredient sufficient to provide the desired result; for example, from about 0.001% to about 20% weight active ingredient and forming the mixture into a paste by the addition of about 1% to 5% of a water based binder such as agar. The paste-like mixture may be applied as is or may be packed into a housing such as a hollowed out wooden dowel or a plastic tube or bait station. In other embodiments, sheets of paper or cardboard can be sprayed with or dipped in a diluted formulation containing the active ingredient. Baits are a preferable embodiment of the present invention.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

The method of applying a compound of Formula (I) to combat termites comprises applying the compound, conveniently in a composition comprising the compound of Formula (I) and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected—i.e., the dosage to which the termite has access—is of the order of 0.001 to 1.0% based on the total weight of the composition, though under some circumstances the effective concentration may be as little as 0.0001% or as much as 2%, on the same basis.

When used to control cockroaches, it is preferred to use the active ingredient in a treated bait or as a surface treatment.

When used to control ants, it is preferred to use the active ingredient in a liquid bait or granular bait.

When used to control termites, it is preferred to use the active ingredient in a cellulose based bait.

When used to control fleas, it is preferred to use the active ingredient on a treated substrate.

Suitable formulations include granular, paste, or dust cockroach bait, SP or WP cockroach and/or flea sprayables, cellulose-based termite baits, liquid or granular ant baits, feed-through or topical animal treatment for fleas.

We claim:

1. A method of controlling cockroaches which comprises delivering an effective amount of a compound of the formula (I)

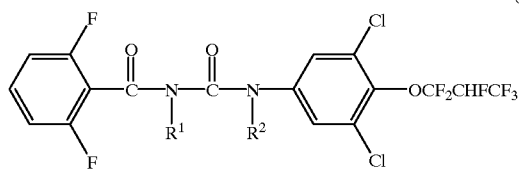

wherein $R^1$ and $R^2$ are H, methyl, or ethyl, to a location where control of cockroaches is desired.

2. A compound of the formula (II)

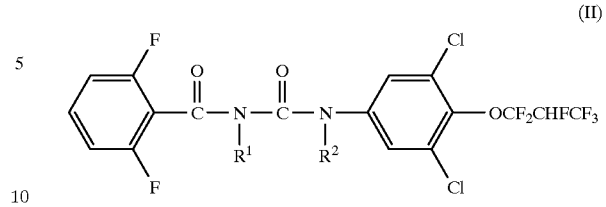

wherein $R^1$ and $R^2$ are H, methyl, or ethyl, provided that at least one of $R^1$ and $R^2$ is methyl or ethyl.

3. A pesticide composition which comprises an effective amount of a compound of claim 2 in combination with a carrier.

4. A cockroach bait comprising a compound of claim 2 in a conventional bait.

* * * * *